United States Patent

Johnston et al.

[11] Patent Number: 6,043,048
[45] Date of Patent: Mar. 28, 2000

[54] RAPID INDUCIBLE BETA-LACTAMASE SCREEN TEST

[75] Inventors: Judith Johnston, Carmichael; Tracy Felland, Sacramento; Shoshana Bascomb, Davis; James H. Godsey, Folsom, all of Calif.

[73] Assignee: Dade MicroScan Inc., West Sacramento, Calif.

[21] Appl. No.: 08/686,434

[22] Filed: Jul. 26, 1996

Related U.S. Application Data

[63] Continuation of application No. 08/324,387, Oct. 17, 1994, abandoned, which is a continuation of application No. 08/109,102, Aug. 19, 1993, abandoned, which is a continuation of application No. 07/924,351, Jul. 31, 1992, abandoned, which is a continuation of application No. 07/696,459, May 6, 1991, abandoned.

[51] Int. Cl.$^7$ .............. C12Q 1/18; C12Q 1/32; C12Q 1/02; C12Q 1/00
[52] U.S. Cl. .............. 435/32; 435/26; 435/29; 435/4; 435/975
[58] Field of Search .............. 435/32, 26, 29, 435/4, 975

[56] References Cited

U.S. PATENT DOCUMENTS

| | | | |
|---|---|---|---|
| 3,509,026 | 4/1970 | Sanders | 435/33 |
| 4,234,683 | 11/1980 | McMillan | 435/32 |
| 4,740,459 | 4/1988 | Chen | 435/32 |
| 5,064,756 | 11/1991 | Carr et al. | 435/32 |
| 5,079,144 | 1/1992 | Carr | 435/32 |

FOREIGN PATENT DOCUMENTS

| | | |
|---|---|---|
| 2 384 022 | 10/1978 | France . |
| 2 128 737 | 5/1984 | United Kingdom . |
| WO 92/11386 | 7/1992 | WIPO . |

OTHER PUBLICATIONS

Sanders et al. Antimicrobial Agents and Chematherapy vol. 15 No. 6 pp. 792–797 (1979.
Sanders et al., *J. Infect. Dis.*, 154:792(1986).
Mett, et al., *Eur. J. Clin.* Microbiol., 7;669(1988).
Jarlov, et al., *Acta Pathol. Microbiol. Immunol. Scand.*, 94:415 (1986).
Pederson, et al., *J. Antimicrob. Chemother.*, 19:101 (1987).
Sanders, et al.; *Euro. J. Clin. Microbiol.*; Clinical Importance of Inducible Beta–Lactamases in Gram–Negative Bacteria; vol. 6, No. 4; pp. 425–437; Aug. 87.
Jorgensen, J.H.; *Chemioterapia*; Susceptibility Test Methods Which May Be Able to Predict the Emergence of Resistance to Newer β–Lactam Antibiotics; vol. 4, No. 1; pp. 7–13; Feb. 85.

*Primary Examiner*—Louise N. Leary
*Attorney, Agent, or Firm*—Lisa V Mueller; Timothy L Tilton; Lois K Ruszala

[57] ABSTRACT

In an assay for determination of beta-lactam antibiotic resistance in a target bacterial strain, the strain is grown in the presence of both a beta-lactamese inducing antibiotic and a beta-lactam indicator antibiotic [which kills or inhibits the growth of bacteria] unable to hydrolyze beta-lactam antibiotics. Growth, indicative of drug resistance in the target strain, is monitored by detecting a fluorophor released by the enzymatic cleavage of a metabolizable fluorogenic compound.

7 Claims, 1 Drawing Sheet

RAPID INDUCIBLE BETA-LACTAMASE SCREEN TEST

This application is a continuation of U.S. Ser. No. 08/324,387, filed Oct. 17, 1994, now abandoned, which is a continuation of U.S. Ser. No. 08/109,102, filed Aug. 19, 1993, now abandoned, which is a continuation of U.S. Ser. No. 07/924,351, filed Jul. 31, 1992, now abandoned, which is a continuation of U.S. Ser. No. 07/696,459, filed May 6, 1991 now abandoned.

BACKGROUND OF THE INVENTION

Antimicrobial susceptibility tests are among the most important tests performed in the clinical microbiology laboratory. Administration of antibiotics to patients whose infections are caused by bacteria resistant to those antibiotics seriously compromises and delays effective therapy. Resistance to antibiotics is mediated by several mechanisms. In the case of antibiotics containing a beta-lactam ring structure, such as the penicillins, cephalosporins, carbapenems, cephamycins, and monobactams, resistance is conferred by beta-lactamases, which hydrolyze the beta-lactam ring, thereby inactivating the antibiotic.

The genes encoding the beta-lactamases may be constitutively expressed by plasmids carried by the bacterial host, or may reside in the bacterial chromosome. Class I beta-lactamases are of the latter type and are induced following exposure to a beta-lactam antibiotic. These enzymes are produced in finite but very low amounts in the uninduced state. Class I beta-lactamases include the cephalosporinases, which inactivate all beta-lactam antibiotics including penicillins, cephalosporins, cephamycins, and monobactams. Virtually all strains of *Citrobacter freundii*, Enterobacter spp., *Moraanella moraanii, Proteus vulgaris*, Providencia spp., *Pseudomonas aeruginosa*, and Serratia spp. contain class 1 beta-lactamases.

It is known that class I beta-lactamases are induced to varying degrees by different beta-lactam antibiotics, as summarized by Sanders, et al., Eur. J. Clin. Microbiol., 6: 435 (1987). This means that some antibiotics such as cefoxitin and imipenem are excellent inducers, resulting in production of high levels of beta-lactamases. Others, however, such as ticarcillin, ceftazidime, mezlocillin, piperacillin, carbenicillin and ceftriaxone are not particularly good inducers of enzyme. Since the level of enzyme is too low to quantitate in the repressed (uninduced) state, assays in the prior art have adopted a format in which beta-lactamase is first induced with an inducing antibiotic, and then the organism is challenged with the indicator antibiotic.

One such assay has been described by Sanders, et al., Antimicrobial Agents and Chemotherapy, 15:792 (1979) for an agar dilution technique. In this assay a Petrie dish is overlayed with agar containing the pregrown target organism. A first disk impregnated with the inducing antibiotic is placed on the agar surface. A second disk impregnated with the indicator antibiotic is placed about 10 millimeters from the first disk. The Petrie dish is incubated for some 18–24 hours.

As the bacterial lawn grows up, the antibiotics diffuse from the disks into the surrounding agar. If the organism is susceptible to the indicator antibiotic, a completely round clear zone of inhibition is observed. If the organism is induced, the zone of inhibition is flattened on the edge between the two antibiotic disks. The explanation for the result is that there is a diffusion race in which the embedded incipient colonies of the target organism closer to the inducing antibiotic become resistant through induction of the protective beta-lactamase before the indicator antibiotic has time to reach them. FIG. 1 of the Example hereinbelow illustrates this test.

Sanders, et al., J. Infect. Dis., 154: 792 (1986) described an alternate method for detection of beta-lactam resistant organisms, in which the target strain is first grown up in the presence of an inducing antibiotic. The cells are collected, lysed, and beta-lactamase activity is measured in the supernatant.

Mett, et al., Eur. J. Clin. Microbiol., 7: 669 (1988) described a relatively rapid test in which bacteria carrying a gene for inducible beta-lactamase expression are inoculated into microtiter plates for determination of the minimum inhibitory concentration. After 4 hours of incubation, a chromogenic beta-lactamase substrate is added and changes in color are monitored over the next three hours of incubation. A similar approach was reported by Jarlov, et al., Acta Pathol. Microbiol. Immunol. Scand., 94: 415 (1986).

There have been several studies in which combinations of inducing and noninducing beta-lactam antibiotics have been utilized. See, for example, Pederson, et al., J. Antimicrob. Chemother., 19: 101 (1987). The object of making these combinations is to assess a synergistic potential of the combinations against particularly intractable bacterial strains.

In general, the current methods of determining beta-lactam susceptibility and resistance, namely, agar dilution, broth microdilution, Kirby-Bauer, all fail to detect drug resistance in certain gram-negative bacteria, as discussed by Jorgensen, Chemiotherapia, 4: 7 (1985). The known methods all require a pregrowth step in which the strain is grown in broth or on a plate under conditions in which the organism is exposed only to the inducing antibiotic. This step is followed by a challenge in the presence of an indicator antibiotic or direct assay of enzymatic activity. These approaches require pure culture inoculation and growth, and involve up to 24 hours incubation.

SUMMARY OF THE INVENTION

In the assays of beta-lactam antibiotic resistance in the prior art, a great deal of time is lost because a growth step is required prior to assay which takes several hours. The assay itself may then require some further several hours of incubation. Even these tests will fail to detect a bonafide resistant organism, because of the very low numbers of a mutant resistant strain which may be present. Accordingly, it is an object of the present invention to provide a rapid and highly reliable assay of beta-lactam antibiotic resistance.

It is a further object to provide a simple assay which requires no handling steps involving direct enzyme assay requiring separate addition of reagents. It is a still further object of the invention to provide an assay which can utilize existing instrumentation to read and interpret results in an automated format.

In the present assay for rapid determination of beta-lactam antibiotic resistance, the target strain in pure culture is inoculated into growth media containing both a beta-lactamase inducing antibiotic and a beta-lactam [nonindicator] antibiotic, which would kill or inhibit it in the uninduced state. A metabolizable fluorogenic compound is added either in the media prior to inoculation, or after a period of growth. A resistant organism or an inoculum containing a resistant organism will grow in the media, whereas a susceptible organism will not grow.

Metabolism of an [ssential] nutrient-containing fluorogenic compound releases the fluorophor which is detected by conventional fluorimetry. A susceptible organism, in which the protective beta-lactamase is not induced, will not grow, and increase in fluorescence of the sample will not be noted.

The present invention also provides a kit comprising one or a plurality of incubation vessels containing a dried, a reconstitutable first inducing beta-lactam antibiotic, a second dried reconstitutable indicator [noninducing] beta-lactam antibiotic, and a metabolizable fluorogenic compound.

DETAILED DESCRIPTION OF THE PREFERRED EMBODIMENT

Figure 1A:
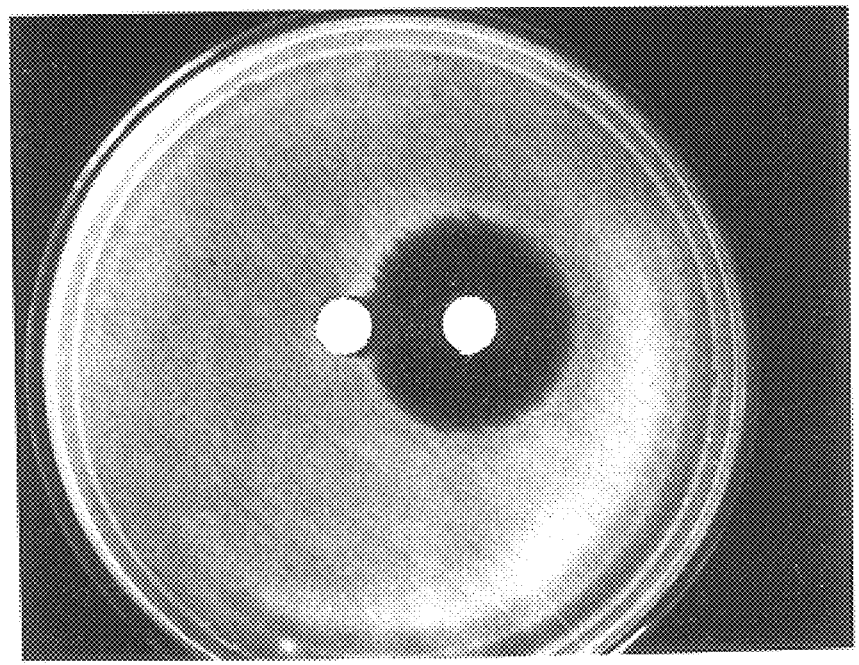
FIG. 1A shows a typical pattern of inhibition around a mezlocillin (Mz) disk.
Figure 1B:
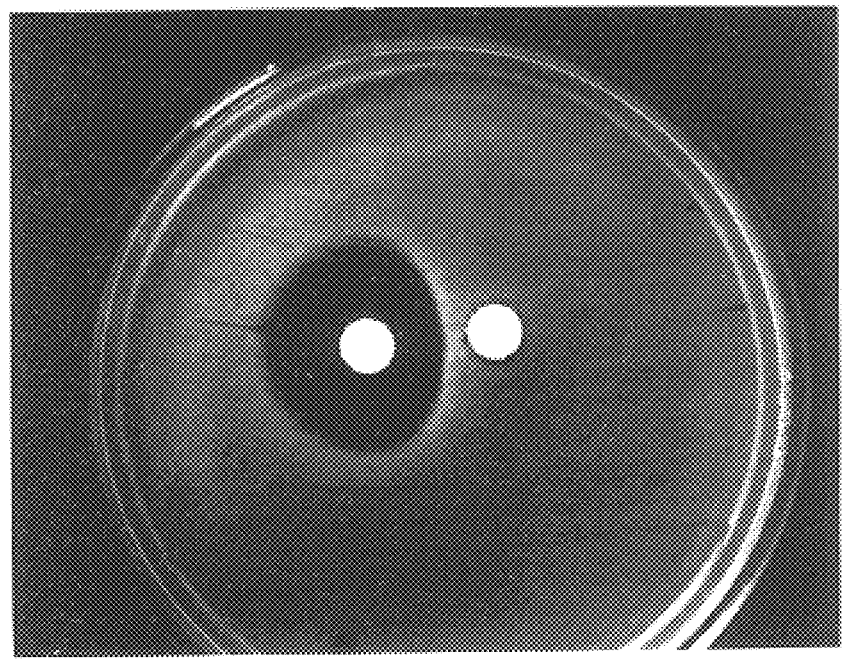
FIG. 1B shows Enterobacter cloacae demonstrating constriction of the zone of inhibition between the Mz and the cefoxitin (FOX) disks.

In the present assay, a bacterial strain of unknown susceptibility to beta-lactam antibiotics is assayed for drug resistance. Since the chromosomally encoded beta-lactamase genes exhibit induced expression, challenge of the organism with the antibiotic directly may yield false susceptibility results. Also, the patient sample may contain a number of different organisms, and within even an individual isolate, there may be small numbers of mutant organisms, either constitutively positive or negative for the enzyme, or which are mutant for the antibiotic binding site.

The sample is inoculated into growth media containing both an inducing and an indicator noninducing beta-lactam antibiotic. Applicants consider adding growth media already inoculated with a sample to the inducing and indicator antibiotics either dried or resuspended in a compatible buffer to be the equivalent of inoculating growth media containing the two antibiotics, so long as both drugs are present simultaneously during incubation.

Inoculations should result in a final concentration of organisms of from about $1\times10^5$ CFU/ml to $1\times10^6$ CFU/ml. The medium be any [defined] medium capable of supporting the growth of the species of organism so inoculated. For most gram-negative isolates, Mueller-Hinton broth is preferred. The inducing antibiotic is selected from the group comprising the beta-lactam antibiotics which have been shown empirically to cause induction of the beta-lactamase gene with concomitant high level expression of the enzyme.

The scientific basis for the observation that some of the beta-lactam antibiotics are better inducers of beta-lactamase is not presently known. One possible mechanism is a greater affinity of a particular drug for the repressor protein, or a binding interaction which enhances the conformational effect on the repressor which controls expression of the operon. There does not, however, appear to be a correlation between the inducer function and the minimum inhibitory concentration (MIC).

Inducer antibiotics include cefoxitin, imipenem, sulbactam and clavulanic acid; cefoxitin is preferred. The concentration of inducer may be varied; 0.1–20 mcg/ml is the general range of concentration with 1.0 to 10 mcg/ml being preferred. Indicator antibiotics include ticarcillin, ceftazidime, mezlocillin, piperacillin, carbenicillin, and ceftriaxone; ticarcillin and ceftazidime are preferred. The concentration of indicator may also be varied; 0.1–30 mcg/ml is the general range of concentration with 1.0 to 15.0 mcg/ml being preferred.

Other combinations of antibiotics having inducer and indicator properties may be selected from the groups of beta-lactam antibiotics set forth in Table 1 hereof. The exact concentrations for the respective antibiotics must be determined empirically, but the essential element of the present method is that the inducer and indicator drugs be present simultaneously during the incubation step. In general, the assay should be conducted at or near the minimum inhibitory concentration of the indicator drug, which is determined empirically by running a drug dilution series in the presence of the indicator antibiotic.

It may also be found desirable to combine two or more inducer and indicator antibiotics in the media to be inoculated. Such combinations are considered to be the equivalents of pairwise combinations. The essential element is that both the inducer and indicator functionalities be present simultaneously during incubation.

It is preferred that a metabolizable fluorogenic compound be incorporated into the growth medium into which the patient sample is inoculated. Known fluorogenic compounds include alanine-7-amido-4-methyl-coumarin and 4-methylumbelliferone [compounds]. Alanine-7-amido-4-methyl-coumarin is preferred because most gram-negative organisms are capable of [secreting] an enzyme capable of hydrolyzing the alanine [as a source of the metabolite]. Cleavage of the alanine results in release of the fluorophor, which can be detected by conventional fluorimetry. In this assay format a two-fold increase in fluorescence compared to controls is deemed a positive test. Incorporating the fluorogenic compound during incubation is desirable since the cumulative effect of the release of the fluorophor gives an earlier positive determination. Bacterial growth can be measured in other ways, such as by nephelometry, spectroscopy, pH change, or by determination of metabolic by-products. By these parameters, a two-fold increase of signal over backround is deemed a positive test.

The present invention also contemplates a kit containing reagents ready for use. The kit comprises one or a plurality of incubation vessels containing dried reconstitutable antibiotics comprising at least one inducing beta-lactam antibiotic, at least one beta-lactam indicator noninducing beta-lactam antibiotic, and a metabolizable fluorogenic compound. In preparing the incubation vessels it was found that air drying, e.g. passing air over the vessel compartments is preferable to lyophilizing because the antibiotics are more readily reconstituted with a buffer or growth media after drying. Air drying is also less expensive than freeze drying.

Any instrument capable of measuring fluorescence may be utilized in practicing the present assay. Preferably an instrument is used which can monitor fluorescence during the course of the incubation. A system having a heated chamber maintained at physiological temperature, which can simultaneously monitor fluorescence of at least 96 samples contained in a microtiter plate is especially desirable. One such system is the Baxter autoSCAN®-W/A instrument.

Other advantages of the present assay will be apparent from the Example which follows:

EXAMPLE

A total of 459 gram-negative organisms were tested on the rapid β-lactamase screen panel. Of these, 299 organisms belong to species known to contain class 1 β-lactamases (Group 1, Table 1); the remaining 160 isolates represent species whose β-lactamase genes are not known to be inducible (Group 2, Table 2).

Table 3 gives examples of mutant and wild-type strains. Results for *Ent. cloacae* and *Ps. aeruainosa* with ceftazidime (Caz) and ceftazidime plus cefoxitin (Caz w/Cfx) are shown. Results for *Cit. freundii* and *Ent. cloacae* with ticarcillin (Ti) and with ticarcillin plus cefoxitin (Ti w/Cfx) are also given. The results for a mutant (mut) strain, *Ent. cloacae* (#498), are given where the percent fluorescence in the control wells were already high; therefore, induction was undetectable. Typical positive induction results are given for a wild-type (w.t.) strain, *Ent. cloacae* #20-8, where the percent fluorescence in Caz w/Cfx was 47% versus 5% in Caz alone. Even though cefoxitin was added to all concentrations of ceftazidime and ticarcillin, induction was frequently observed only in the wells containing the lowest concentrations of the antibiotics. Similar inductions can be observed in all examples of Table 3.

Summaries of induction of β-lactamase, expressed as a constriction of the zone of inhibition to mezlocillin, as tested by the K-B method, or increased resistance to ticarcillin, ceftazidime or to both antibiotics (rapid β-lactamase screen) are given in Table for organisms of groups 1 and 2. The overnight K-B (Kirby-Bauer disk approximation test) method detected β-lactamase induction in 109/230 isolates (47%). The rapid method of the present invention detected induction of β-lactamase in 68/230 isolates (29.6%). Induction of resistance to both ticarcillin and ceftazidime, or to either was observe with *Cit. freundii, Ent. cloacae* and *Ent. aerogenes*. Induction of resistance to ceftazidime only was observed with *Ps. aeruginosa* isolates. The rapid method could detect induction in these four species as successfully as the overnight method. The rapid method could not detect induction in *Prt. vulgaris, Ser. marcescens* and *Aer. hydrophila*. As would be expected, both methods did not detect induction in isolates of group 2 taxa.

The disk constriction method has been designed to help predict which organisms may develop in vitro resistance to β-lactam antibiotics, thereby to improve the choice of drug for therapy. However, expression of the genes both in vitro or in vivo is not completely understood. Although it is assumed that resistance to all β-lactam antibiotics is induced, the in vitro expression of such resistance to the various antibiotics is not identical. Both choice of inducer and choice of test-antibiotic may affect the results. Using the reference method, cefoxitin, clavulanic acid and imipenem were shown to be good inducers. In this method, organisms are preincubated with inducer, followed by centrifugation, lysis of the bacterial cells and detection of β-lactamase induction by very sensitive detection of enzymatic activity towards cephalothin.

Using the K-B method cefoxitin has been shown to be a good inducer and many of the β-lactam antibiotics have been shown to be suitable indicators for detection of induction. The present study shows that cefoxitin is a good inducer for ca. 50% of the strains of *Ent. cloacae* and *Ps. aeruginosa*, induction being detected by both conventional and rapid methods. Induction was detected in *Xan. maltophilia* by the rapid method only. Induction was detected in *Aer. hydrophila, Ser. marcescens* and members of the tribe Proteae by the disk method only. These isolates were susceptible to cefoxitin and the concentration of the antibiotics used in the rapid β-lactamose screen test did not allow growth in sufficient quantity to be detected by the rapid method.

The rapid method was comparable to the disk approximation test in the detection of induction in *Cit. freundii, Ent. aerogenes, Ent. cloacae*, and *Ps. aeruginosa*, as well as showing no induction of any isolates of taxa in Group 2. This rapid method was better than the K-B disk approximation method for detection of induction in *Xan. maltophilia*. The isolates in which induction could not be detected could be divided into two categories. Those which were already resistant to the indicator antibiotics and further induction was undetectable, and those in which, even though susceptible to the indicator, induction could not be demonstrated.

The described method is the first successful rapid detection of inducible class 1 β-lactamases. The rate of success for the majority of taxa tested is comparable to that of the overnight method.

TABLE 1

The β-Lactam Family of Antibiotics[a]

| Penicillins | Cephalosporins | Cephamycins |
|---|---|---|
| Benzylpenicillin | Cephalothin | Cefoxitin |
| Methicillin | Cefamandole | Cefotetan |
| Ampicillin | Cefuroxime | Cefmetazole |
| Carbenicillin | Cefotaxime | |
| Mezlocillin | Ceftriaxone | |
| Piperacillin | Ceftazidime | |
| Carbapenems | Monobactams | |
| Imipenem | Aztreonam | |

[a]Limited examples in each group are given

TABLE 2

Group 1

| Class 1 β-lactamase Producers | Total # Tested | Distribution and numbers of isolates tested | |
|---|---|---|---|
| | | Wild-Types | Mutants |
| *Aeromonas hydrophila* group | 15 | 15 | 0 |
| *Citrobacter freundii* | 48 | 35 | 13 |
| *Enterobacter aerogenes* | 25 | 19 | 6 |
| *Enterobacter agglomerans* | 4 | 4 | 0 |
| *Enterobacter cloacae* | 30 | 20 | 10 |
| *Morganella morganii* | 25 | 19 | 6 |
| *Proteus vulgaris* | 20 | 16 | 2 |
| *Providencia rettgeri* | 16 | 16 | 0 |
| *Providencia stuartii* | 16 | 10 | 6 |
| *Pseudomonas aeruginosa* | 32 | 26 | 6 |
| Other Pseudomonas spp. | 17 | 4 | 13 |
| *Serratia liquefaciens* | 20 | 20 | 0 |
| *Serratia marscescens* | 25 | 20 | 5 |
| *Xanthomonas maltophilia* | 6 | 4 | 2 |
| Total | 299 | 230 | 69 |

Group 2

| Other Stains Tested: | Total # Tested |
|---|---|
| Acinetobacter spp. | 14 |
| Citrobacter amalonaticus | 12 |
| Citrobacter diversus | 13 |
| Escherichia coli | 25 |
| Klebsiella oxytoca | 20 |
| Klebsiella pneumoniae | 20 |
| Proteus mirabilis | 24 |
| Salmonella/Arizona | 6 |
| Salmonella paratyphi | 4 |
| Salmonella typhi | 6 |
| Shigella spp. | 16 |
| Total | 160 |

TABLE 3

Induction of β-lactamases on the Rapid β-lactamase Screen

| | Percent fluorescence at each concentration of antibiotic Ceftazidime (mcg/ml) | | | | | |
|---|---|---|---|---|---|---|
| | 1 | 2 | 4 | 6 | 16 | 32 |
| *Ent. cloacae* #498 (mut.) | | | | | | |
| Caz alone | 96 | 90 | 100 | 97 | 100 | 74 |
| Caz w/Cfx | 100 | 100 | 100 | 100 | 98 | 77 |
| *Ent. cloacae* #20-8 (w.t.) | | | | | | |
| Caz alone | 5 | 5 | 5 | 4 | 4 | 3 |
| Caz w/Cfx | 47 | 7 | 5 | 5 | 4 | 3 |
| *Ps. aeruginosa* #55-9 (w.t.) | | | | | | |
| Caz alone | 24 | 8 | 7 | 5 | 6 | 7 |
| Caz w/Cfx | 69 | 37 | 11 | 8 | 8 | 7 |

| | Ticarcillin (mcg/ml) | | | |
|---|---|---|---|---|
| | 8 | 16 | 32 | 64 |
| *Ent. cloacae* #543 (mut.) | | | | |
| Ti alone | 100 | 100 | 100 | 90 |
| Ti w/Cfx | 100 | 100 | 100 | 83 |
| *Cit. freundii* #539 (w.t.) | | | | |
| Ti alone | 15 | 15 | 14 | 12 |
| Ti w/Cfx | 89 | 75 | 67 | 26 |
| *Ent. cloacae* #20-8 (w.t.) | | | | |
| Ti alone | 4 | 4 | 5 | 3 |
| Ti w/Cfx | 88 | 37 | 8 | 3 |

Legend: Caz = ceftazidime; Caz w/Cfx = ceftazidime plus cefoxtin; Ti = ticarcillin; Ti w/Cfx = ticarcillin plus cefoxitin; w.t. = wild-type strain; mut = mutant strain.

TABLE 4

Number of Strains Induced in Each Antibiotic Containing Cefoxitin Group 1, Class 1 b-lactamase, Producers

| | NUMBER OF STRAINS INDUCED | | | | | |
|---|---|---|---|---|---|---|
| Organisms: | Total # Strains | Ti & Caz | Ti Only | Caz Only | Total | K-B |
| *Cit. freundii* | 46 | 11 | 5 | 1 | 17 | 15 |
| *Ent. cloacae* | 30 | 12 | 0 | 3 | 15 | 14 |
| *Ps. aeruginosa* | 32 | 1 | 0 | 15 | 16 | 15 |
| *Ent. aerogenes* | 25 | 4 | 3 | 1 | 8 | 6 |
| *Prt. vulgaris* | 20 | 1 | 0 | 1 | 2 | 9 |
| *Mor. morganii* | 25 | 2 | 0 | 0 | 2 | 15 |
| *Ser. marcescens* | 25 | 0 | 0 | 0 | 0 | 15 |
| *Ent. agglomerans* | 4 | 0 | 0 | 0 | 0 | 0 |
| *Prv. rettgeri* | 16 | 0 | 0 | 0 | 0 | 0 |
| *Prv. stuartii* | 16 | 0 | 0 | 0 | 0 | 2 |
| *Aeromonas hydrophila* grp | 15 | 0 | 0 | 0 | 0 | 13 |
| *Ser. liquefaciens* | 20 | 0 | 1 | 0 | 1 | 1 |
| *Xan. maltophilia* | 6 | 1 | 1 | 2 | 4 | 0 |
| Other Pseudomonads | 17 | 0 | 1 | 2 | 3 | 4 |
| | 299 | 32 | 11 | 25 | 68 | 109 |
| Group 2 | | | | | | |
| *Kleb. pneumoniae* | 20 | 0 | 0 | 0 | 0 | 0 |
| *E. coli* | 25 | 0 | 0 | 0 | 0 | 0 |
| *Kleb. oxytoca* | 20 | 0 | 0 | 0 | 0 | 0 |
| *Prt. mirabilis* | 24 | 0 | 0 | 0 | 0 | 0 |
| *Cit. amalonaticus* | 12 | 0 | 0 | 0 | 0 | 0 |
| *Cit. diversus* | 13 | 0 | 0 | 0 | 0 | 0 |
| Salmonella/Arizona | 6 | 0 | 0 | 0 | 0 | 0 |
| *Sal. typhi* | 6 | 0 | 0 | 0 | 0 | 0 |
| *Sal. paratyphi* | 4 | 0 | 0 | 0 | 0 | 0 |
| *Shigella* spp. | 16 | 0 | 0 | 0 | 0 | 0 |
| *Acinetobacter* spp. | 14 | 0 | 0 | 0 | 0 | 0 |
| | 160 | 0 | 0 | 0 | 0 | 0 |

What is claimed is:

1. An assay for the rapid determination of resistance of a bacterial strain to a beta-lactam antibiotic comprising:
   inoculating a bacterial strain into a growth medium containing simultaneously at least one beta-lactamase inducing antibiotic, at least one beta-lactamase indicator antibiotic and at least one metabolizable fluorogenic compound which is enzymatically hydrolyzable to yield a fluorophor;
   incubating for a sufficient amount of time to allow the bacterial strain to grow;
   measuring the growth of the bacterial strain by detecting the fluorophor; and
   determining whether the bacterial strain is resistant to the beta-lactam antibiotic based on the detection of the fluorophor.

2. An assay for the rapid determination of resistance of a bacterial strain to a beta-lactam antibiotic comprising:
   inoculating a bacterial strain into a growth medium containing simultaneously at least one beta-lactamase inducing antibiotic and at least one beta-lactamase indicator antibiotic;
   incubating for a sufficient amount of time to allow the bacterial strain to grow;
   adding at least one metabolizable fluorogenic compound which is enzymatically hydrolyzable to yield a fluorophor to the growth medium;
   incubating for a sufficient amount of time to allow the fluorogenic compound to react with the bacterial strain;
   measuring the growth of the bacterial strain by detecting the fluorophor; and
   determining whether the bacterial strain is resistant to the beta-lactam antibiotic based on the detection of the fluorohor.

3. The assay of claim 1 or claim 2 wherein the inducing antibiotic is selected from the group consisting of cefoxitin, imipenem, sulbactam and clavulanic acid.

4. The assay of claim 1 or claim 2 wherein the indicator antibiotic is selected from the group consisting of ticarcillin, ceftazidime, mezlocillin, piperacillin, carbenicillin and ceftriaxone.

5. A kit for the rapid determination of resistance of a bacterial strain isolated from a patient to a beta-lactam antibiotic comprising:
   a compartment containing at least one dried reconstitutable inducing beta-lactam antibiotic, at least one dried constitutable indicator antibiotic, and at least one metabolizable fluorogenic compound.

6. The kit of claim 5 wherein a bacterial strain and a growth medium are inoculated into each compartment.

7. The kit of claim 6 wherein the inoculation of the growth medium rehydrates each compartment.

* * * * *